United States Patent
Gilmore et al.

(10) Patent No.: US 9,440,899 B2
(45) Date of Patent: Sep. 13, 2016

(54) PURIFICATION METHOD

(71) Applicant: Rohm and Haas Electronic Materials LLC, Marlborough, MA (US)

(72) Inventors: Christopher D. Gilmore, Watertown, MA (US); Chi-Wan Lee, Grafton, MA (US); Peter Trefonas, III, Medway, MA (US); William Williams, III, Ipswich, MA (US); Qiuzhe Xie, Westborough, MA (US)

(73) Assignee: Rohm and Haas Electronic Materials LLC, Marlborough, MA (US)

( * ) Notice: Subject to any disclaimer, the term of this patent is extended or adjusted under 35 U.S.C. 154(b) by 3 days.

(21) Appl. No.: 14/569,813

(22) Filed: Dec. 15, 2014

(65) Prior Publication Data

US 2016/0168064 A1  Jun. 16, 2016

(51) Int. Cl.
*C07C 69/28* (2006.01)
*C07C 69/12* (2006.01)
*C07C 69/92* (2006.01)
*C07C 41/42* (2006.01)
*B01D 3/00* (2006.01)
*C07C 67/40* (2006.01)
*C07C 43/13* (2006.01)
*C07C 41/44* (2006.01)

(52) U.S. Cl.
CPC ............ *C07C 41/42* (2013.01); *B01D 3/009* (2013.01); *C07C 41/44* (2013.01); *C07C 43/13* (2013.01); *C07C 67/40* (2013.01); *C07C 69/12* (2013.01)

(58) Field of Classification Search
CPC ........ C07C 69/28; C07C 69/12; C07C 69/92

USPC .................. 558/277; 560/98, 234
See application file for complete search history.

(56) References Cited

U.S. PATENT DOCUMENTS

| | | | | |
|---|---|---|---|---|
| 2,072,806 A | * | 3/1937 | Wood, Jr. | ............... C07C 29/74 518/728 |
| 2,476,053 A | * | 7/1949 | Lippincott | ............. C07C 69/28 560/234 |
| 2,872,478 A | * | 2/1959 | Wechsler | ............... C07C 69/12 558/277 |
| 2,923,733 A | * | 2/1960 | Walker | .................... C07C 29/92 560/98 |
| 5,723,024 A | | 3/1998 | Berg | |
| 6,846,961 B2 | * | 1/2005 | Teles | .................... C07F 15/065 568/678 |

FOREIGN PATENT DOCUMENTS

| | | | |
|---|---|---|---|
| CN | 101985418 A | * | 3/2011 |
| EP | 138153 A2 | | 4/1985 |
| WO | 03022785 A2 | | 3/2003 |

OTHER PUBLICATIONS

Anne M. Pautard, et al, "Chemoselective Banzoylations of 1,2-Diols. Reactivity Comparisons of Reagents. Triphenylphosphine-Benzoyl Peroxide and Triphenylphosphine-Diethyl Azodicarboxylate-Benzoic Acid", J. Org Chem., 1988, pp. 2300-2303, vol. 53.

* cited by examiner

*Primary Examiner* — Sudhakar Katakam
*Assistant Examiner* — Everett White
(74) *Attorney, Agent, or Firm* — S. Matthew Cairns

(57) ABSTRACT

A method of separating a secondary alcohol compound from a primary alcohol compound using selective acylation is provided.

12 Claims, No Drawings

PURIFICATION METHOD

The present invention relates generally to the field of separation of organic compounds, and more particularly to the separation of alcohol compounds.

Distillation is a common technique used to separate organic compounds, which relies on a difference in boiling points of the compounds to be separated. As the difference in boiling points of the compounds to be separated becomes smaller, enhanced distillation techniques, such as packed distillation columns, Vigreux columns, and the like, are used to effect better separation of the compounds. In the case of compounds having very similar boiling points, such as the separation of one isomer from another, such distillation techniques are effective to remove a majority of the undesired compound, but often a significant amount of the undesired compound remains with the desired compound.

Propylene glycol methyl ether acetate (PGMEA) is a common solvent used in the electronics industry. PGMEA exists in two isomeric forms, alpha and beta. The beta-isomer has been reported to have teratogenic activity, and certain regulations require ≤3000 ppm (0.3 wt %) of this isomer be present. There is a desire in the electronics industry to remove as much of the beta-isomer of PGMEA as possible. PGMEA is prepared by the acylation of the corresponding alcohol, propylene glycol methyl ether (PGME), which also exists as alpha- and beta-isomers. The difference in boiling points of the alpha- and beta-isomers of PGME is approximately 10° C., which presents considerable challenges to removing substantially all of the unwanted beta-isomer by distillation alone on a commercial scale, even with enhanced distillation techniques.

U.S. Pat. No. 5,723,024 discloses a process for separating 2-methyl-1-propanol from its isomer 1-butanol by extractive distillation using an extractive agent such as ethyl benzene and amyl acetate, among others. The difference in boiling points between 2-methyl-1-propanol and 1-butanol is 10° C. This process provides enhanced volatility of the 2-methyl-1-propanol, with a vapor phase composition ratio of 2-methyl-1-propanol to 1-butanol of about 2:1 and a ratio of about 1:1 in the liquid phase composition. Not only does this process introduce another potential impurity (the extractive agent) into the desired material, the composition of the vapor phase is still very high in the unwanted 1-butanol isomer. The industry is still in need of an effective procedure for separating alcohol compounds having substantially similar boiling points, that is a difference in boiling points of ≤15° C. at atmospheric pressure.

The present invention provides a method of separating a secondary alcohol compound from a primary alcohol compound comprising: providing a mixture of a secondary alcohol compound and a primary alcohol compound; reacting the mixture with an amount of an acylating agent of formula 1 sufficient to acylate the primary alcohol compound in the presence of an acid catalyst to form a partially acylated mixture comprising the secondary alcohol compound and acylated primary alcohol compound,

(1)

wherein $R^1$ is a bulky group; Y is chosen from halogen, OH, and —O—C(O)—$R^1$; separating the secondary alcohol compound from the acylated primary alcohol compound; wherein the acylation step is free of inorganic and enzymatic catalysts.

As used throughout this specification, the following abbreviations shall have the following meanings, unless the context clearly indicates otherwise: ° C.=degree Celsius; g=gram; L=liter; mL=milliliter; mm=millimeter; and DI=deionized. All amounts are percent by weight ("wt %") and all ratios are molar ratios, unless otherwise noted. All numerical ranges are inclusive and combinable in any order, except where it is clear that such numerical ranges are constrained to add up to 100%. The articles "a", "an" and "the" refer to the singular and the plural. "Alkyl" refers to linear, branched and cyclic alkyl unless otherwise specified. "Aryl" refers to aromatic carbocycles and aromatic heterocycles.

In the present invention, a secondary alcohol compound is separated from a primary alcohol compound by first acylating the primary alcohol compound, and then separating secondary alcohol compound from the acylated primary alcohol compound, wherein the acylation step is free of inorganic catalysts, enzymatic catalysts, and mixtures thereof. In the present process, a mixture of a secondary alcohol compound and a primary alcohol compound is provided; the mixture is reacted with an amount of an acylating agent of formula 1 sufficient to acylate the primary alcohol compound in the presence of an acid catalyst to form a partially acylated mixture comprising the secondary alcohol compound and acylated primary alcohol compound,

(1)

wherein $R^1$ is a bulky group; Y is chosen from halogen, OH, and —O—C(O)—$R^1$; and the secondary alcohol compound is separated from the acylated primary alcohol compound; wherein the acylation step is free of inorganic and enzymatic catalysts.

The present process is useful for separating any secondary alcohol compound from a primary alcohol compound, and any suitable mixture primary alcohol compound and secondary alcohol compound may be used. Preferably, the primary alcohol compound and secondary alcohol compound have substantially similar boiling points, that is, a difference in boiling points of ≤15° C. (at atmospheric pressure), more preferably a difference in boiling points of ≤12° C., and even more preferably a difference of ≤10° C. It is preferred that the primary alcohol compound and the secondary alcohol compound are isomers. Preferably, the mixture of the primary alcohol compound and the secondary alcohol compound comprises a majority of the secondary alcohol compound and a minority of the primary alcohol compound. More preferably, the mixture comprises ≥95 wt % of the secondary alcohol compound, still more preferably ≥98 wt % of the secondary alcohol compound, and yet more preferably ≥99 wt % of the secondary alcohol compound. Preferably, the secondary alcohol and primary alcohol compounds are isomers of a $C_{3-30}$ hydrocarbyl alcohol, and more preferably the $C_{3-30}$ hydrocarbyl alcohol has a $C_{1-10}$ hydrocarbyl ether moiety. Most preferably, the mixture of alcohol compounds is a mixture of 2-methoxypropan-1-ol and 1-methoxypropan-2-ol.

Suitable acylating agents useful in the present process are carboxylic acids, carboxylic acid anhydrides and acyl halides. Such acylating agents have the formula (1)

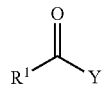

(1)

wherein $R^1$ is a bulky group; Y is chosen from halogen, OH, and —O—C(O)—$R^1$. Preferably, Y is OH or —O—C(O)—$R^1$, and more preferably Y is —O—C(O)—$R^1$. When Y is halogen, it is preferred that Y is chlorine. As used herein, "bulky group" refers to any branched $C_{4-20}$ alkyl, $C_{5-20}$ cycloalkyl, substituted $C_{5-20}$ cycloalkyl, $C_{6-20}$ aryl, and substituted $C_{6-20}$ aryl. By "substituted" it is meant that one or more hydrogens are replaced with one or more substituents chosen from $C_{1-10}$ alkyl, $C_{1-10}$ alkoxy, CN, OH, and halogen. Preferably, $R^1$ is chosen from cyclopentyl, cyclohexyl, cycloheptyl, cyclooctyl, adamantyl, methyladamantyl, tert-butyl, neopentyl, 2-methyl-but-2-yl, 2,4-dimethylpent-3-yl, phenyl, methylphenyl, dimethylphenyl, trimethylphenyl, nitrophenyl, diphenylmethyl, naphthyl, and pyrenyl. Such acylating agents are generally commercially available or may be prepared by procedures well known in the art. Such acylating agents may be used as is or may be further purified. The acylating agent is used in an amount sufficient to acylate the primary alcohol compound, and preferably an amount sufficient to acylate substantially all (≥99%) of the primary alcohol compound. It is preferred that the acylating agent is present in an amount that is 1.5 times the molar amount of the primary alcohol compound, and more preferably ≥2 times the molar amount of the primary alcohol compound, such as 2.5, 3, 3.5, 5, 10 or more times the molar amount of the primary alcohol compound. When a relatively minor amount (such as from 0.001 to 5 wt %) of primary alcohol compound is present in the mixture of alcohol compounds, it is preferred that the acylating agent is present in an amount of from 0.01 to 20 mol % based on the total moles of the primary and secondary alcohol compounds, and more preferably from 0.01 to 10 mol %.

Any acid which catalyzes the acylation of the primary alcohol may be used in the present process. Preferably, the acid catalyst is chosen from a mineral acid, an alkanesulfonic acid, an arylsulfonic acid, and a carboxylic acid. Mixtures of acids may be used. Suitable alkanesulfonic acids include, but are not limited to, methanesulfonic acid, ethanesulfonic and propanesulfonic acid. Suitable arylsulfonic acids include, but are not limited to, phenylsulfonic acid, tolylsulfonic, and phenolsulfonic acid. Exemplary carboxylic acids include, but are not limited to, trifluoroacetic acid, trimethylacetic acid, and the like. Mineral acids are preferred. Exemplary mineral acids include, but are not limited to, sulfuric acid, nitric acid, hydrohalogen acids such as hydrochloric acid, periodic acid, perchloric acid, and the like. Preferred mineral acids are sulfuric acid and hydrochloric acid. Preferably, the acid catalyst is present in an amount of 0.05 to 10 mole equivalents of the acylating agent, more preferably from 0.1 to 10 mole equivalents, and yet more preferably from 0.1 to 5 mole equivalents.

The mixture of the primary alcohol compound and the secondary alcohol compound is reacted with the acylating agent in the presence of the acid catalyst to form a partially acylated mixture. If the mixture of primary and secondary alcohol compounds is a liquid, the acylating agent and acid catalyst may simply be added to the alcohol compound mixture in a suitable vessel and the contents allowed to react. Alternatively, but less preferably, an organic solvent may be used to facilitate the acylation of the primary alcohol compound. If such optional organic solvent is used, such solvent should not react with the acylating agent and should not interfere with the separation of the secondary alcohol compound. Preferably, the reaction mixture is heated to form the acylated primary alcohol compound. The reaction mixture may be heated at any suitable temperature, up to reflux, and preferably it is heated at reflux. While not wishing to be bound by theory, it is believed that the primary alcohol compound is preferentially acylated over the secondary alcohol compound. Thus, the partially acylated mixture comprises acylated primary alcohol compound, and may further comprise acylated secondary alcohol compound. Preferably, substantially all (≥98%) of the primary alcohol compound is acylated, and more preferably ≥99% of the primary alcohol compound is acylated. In the present process, the primary alcohol compound is acylated, a portion of the secondary alcohol compound may be acylated, and at least a portion of the secondary alcohol is not acylated. The acylation step of the present process is performed without the use of inorganic catalysts, enzymatic catalysts, or any combination thereof. As used herein, "inorganic catalysts" refers to metal catalysts, such as metal oxides, metal alloys, and the like, and does not include mineral acids.

Following acylation of the primary alcohol compound, the secondary alcohol compound is separated from the acylated primary alcohol compound. The secondary alcohol compound is also separated from any acylated secondary alcohol compound. Any suitable separation technique may be used, such as one or more of distillation, column chromatography, or crystallization. Such separation techniques are well-known to those skilled in the art. The acylated primary alcohol compound has a higher boiling point than the primary alcohol compound, thus providing a larger difference in boiling points, and making the separation of the secondary alcohol compound easier. There is no requirement for a particular difference in boiling points between the acylated primary alcohol compound and the non-acylated secondary alcohol compound, provided that such difference is sufficient to separate the secondary alcohol compound from the acylate primary alcohol compound. Suitable difference in boiling points between the acylated primary alcohol compound and the non-acylated secondary alcohol compound ≥1° C., preferably ≥5° C., more preferably ≥10° C., still more preferably ≥25° C., and even more preferably ≥50° C. While there is no particular upper limit of such boiling point difference, an exemplary upper limit is 250° C. Accordingly, the difference in boiling points between the acylated primary alcohol compound and the non-acylated secondary alcohol compound may suitably be from 1 to 250° C., preferably from 5 to 250° C., more preferably from 10 to 250° C., and yet more preferably from 25 to 250° C. Alternatively, the acylated primary alcohol may have different affinity for column packing materials as compared to the primary alcohol compound, making separation of the secondary alcohol compound from the acylated primary alcohol compound by column chromatography possible. Preferably, the secondary alcohol compound is separated from the acylated primary alcohol compound by fractional distillation.

The separated secondary alcohol compound is substantially free of the primary alcohol compound, that is, it contains ≤0.5 wt % of the primary alcohol, preferably ≤0.3 wt %, more preferably ≤0.1 wt %, even more preferably ≤100 ppm (by weight), and yet more preferably ≤10 ppm of the primary alcohol, such as from 0 to 10 ppm, as determined by gas chromatographic analysis. A suitable gas chromatograph is on an Agilent 6890 gas chromatograph equipped with a flame ionization detector and an Agilent 122-1334 or Agilent HP-INNOWax column More preferably, the secondary alcohol is substantially free of acylated primary alcohol, and even more preferably substantially free of acylated primary alcohol and acylated secondary alcohol. 1-Methoxypropan-2-ol having ≤10 ppm, such as from 0 to 10 ppm, of 2-methoxypropan-1-ol is obtained from a mixture of 2-methoxypropan-1-ol and 1-methoxypropan-2-ol according to the present process. PGME is a starting material in the synthesis of PGMEA. PGME is acylated with 1 to 2 molar equivalents of acetic acid or acetic anhydride with heating at a temperature of 80 to 150° C. Preferably, such acylation step uses 0.05 to 1 wt % of an acid catalyst. Any suitable acid may be used as the acid catalyst, including mineral acids such as hydrohalogen acids such as hydrochloric acid, phosphoric acid, polyphosphoric acid, sulfuric acid, nitric acid, chlorosulfonic acid, and the like, and organic acids such as oxalic acid, citric acid, p-toluenesulfonic acid, methanesulfonic acid, ethanesulfonic acid, propanesulfonic acid, phenylsulfonic acid, phenolsulfonic acid, and the like. Accordingly, when the PGME used to prepare PGMEA has a very low level of undesired beta-isomer (2-methoxypropan-1-ol), the resulting PGMEA has an equally low level of such isomer. Thus, PGMEA having ≤10 ppm, such as from 0 to 10 ppm, of the undesired beta-isomer, 2-methoxypropyl acetate, is obtained from the separated 2-methoxypropan-1-ol according to the present process.

EXAMPLE 1

Commercially available PGME containing both 2-methoxypropan-1-ol and 1-methoxypropan-2-ol was added to a flask, followed by 1 mol % of trimethylacetic anhydride, and an acid catalyst. The reaction was heated to 120° C. and allowed to stir under mild reflux conditions for 72 hours, prior to fractional distillation of the reagent through a Vigreux column packed with glass beads. All distillate collected before a steady reading of 119-121° C. in the distillation head was discarded, and the subsequent fraction was collected for analysis, until a sudden temperature change was noted. Subsequently, the distillate was analyzed against a standard of >99% pure 2-methoxypropan-1-ol by gas chromatography using an Agilent 6890 gas chromatograph, equipped with a flame ionization detector, an Agilent 122-1334 DB-624 60 m×0.53 mm column with helium as the carrier gas (1.5 mL/min), a 1.0 µL injection volume, an injector split ratio of 10:1, and an initial oven temperature of 40° C., a temperature ramp of 2° C./min to 80° C. with an 8 min. hold time followed by a a temperature ramp of 20° C./min to 200° C. with a 5 min. hold time. The results are reported in Table 1. The Control sample was the commercially available PGME itself.

TABLE 1

| Sample | Acid Catalyst | Beta-isomer (ppm) | Reduction in beta-isomer (%) |
|---|---|---|---|
| Control | — | 1178 | — |
| 1 | 0.5 mol % Trimethylacetic acid | 137 | 88 |
| 2 | 10 mol % sulfuric acid | 11 | 99 |
| 3 | 10 mol % hydrochloric acid | 9 | 99.2 |

It is clear from the data in Table 1 that the level of the primary alcohol (beta-isomer) in the distillate from the present process is significantly reduced.

EXAMPLE 2

To a 250 mL round bottomed flask containing a stir bar is added 100 g PGME (1.11 mol, 1.0 equiv) as a mixture of approximately 99.88% of 1-methoxypropan-2-ol (PM-2) and 0.12% of 2-methoxypropan-1-ol (beta-isomer, PM-1). Benzoic anhydride (2.5 g, 11.1 mmol, 0.01 equiv) is next added to the flask, followed by concentrated sulfuric acid (10.9 g, 111.0 mmol, 0.1 equiv). A reflux condenser is affixed to the reaction and it is left to stir for 36 hours in an oil bath set to 115° C. At the end of this interval, the reflux condenser is removed and a vacuum-jacketed Vigreux column filled with glass beads 1 mm in diameter is attached. Atop this, a short path distillation head is placed with a 100 mL receiving flask. The temperature of the oil bath is increased to 130° C., and the first distillate fraction is collected as the major product, within a temperature range of 118-120° C. Analysis of this material indicates that it consists of starting material isomer PM-2 and is substantially free of isomer PM-1. This process is illustrated by the following reaction scheme.

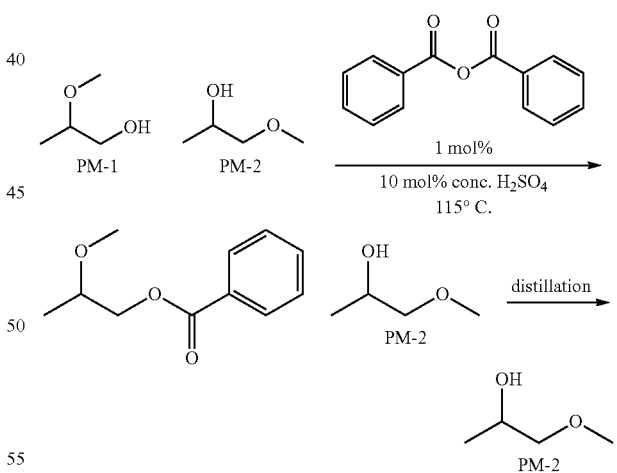

EXAMPLE 3

The procedure of Example 2 is repeated except that the benzoic anhydride is replaced with 2-naphthoic acid (3.8 g, 22.2 mmol, 0.02 equiv). Analysis of the distillate indicates that it is isomer PM-2 and is substantially free of isomer PM-1. This process is illustrated by the following reaction scheme.

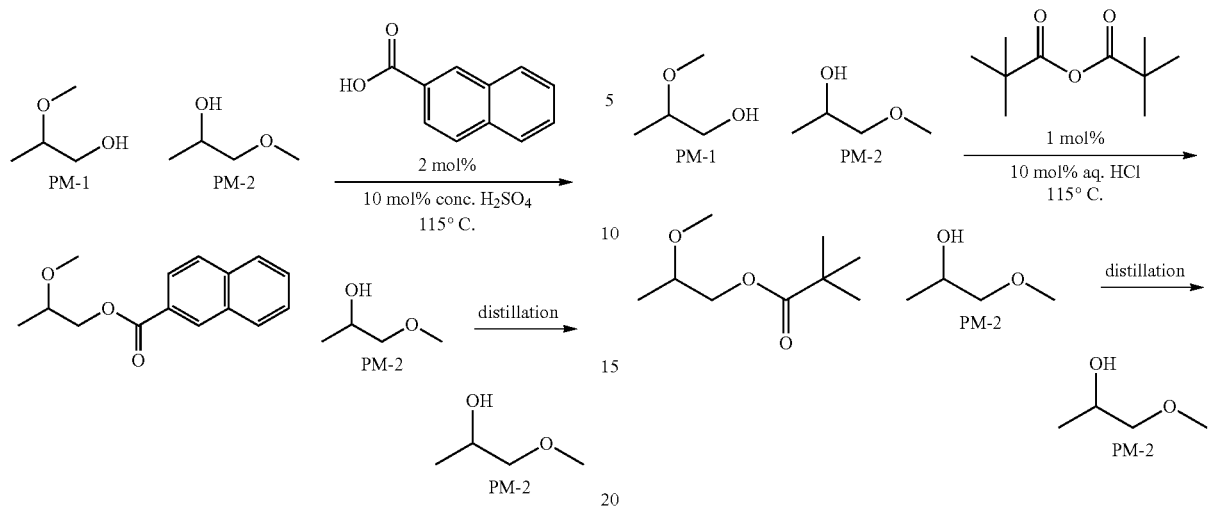

EXAMPLE 4

The procedure of Example 2 is repeated except that the benzoic anhydride is replaced with 1-pyrenecarboxylic acid (5.4 g, 22.2 mmol, 0.02 equiv), and the sulfuric acid catalyst is replaced with 12.1N aqueous hydrochloric acid (9.2 mL, 111.0 mmol, 0.1 equiv). Analysis of the distillate indicates that it is isomer PM-2 and is substantially free of isomer PM-1. This process is illustrated by the following reaction scheme.

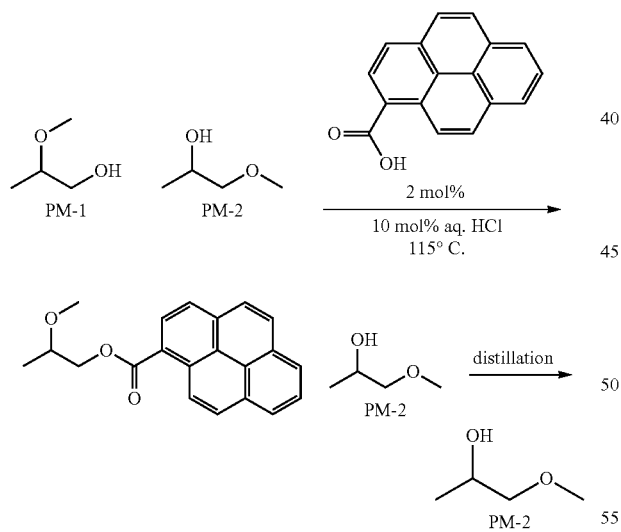

EXAMPLE 5

The procedure of Example 4 is repeated except that the 1-pyrenecarboxylic acid is replaced with trimethylacetic anhydride (2.1 g, 11.1 mmol, 0.01 equiv). Analysis of the distillate indicates that it is isomer PM-2 and is substantially free of isomer PM-1. This process is illustrated by the following reaction scheme.

EXAMPLE 6

Purified PGME Sample 3 from Example 1, containing 9 ppm of the beta-isomer (2-methoxypropan-1-ol), is acylated with acetic acid (1.2 molar equivalents) at a temperature of 80 to 150° C. in the presence of an acid catalyst (0.05 to 1 wt %), such as hydrochloric acid, to provide PGMEA having ≤9 ppm of the beta-isomer (2-methoxypropan-1-acetate).

EXAMPLE 7

The procedure of Example 6 is repeated except that the acetic acid is replaced with acetic anhydride (0.65 molar equivalents) and the acid catalyst is phosphoric acid.

What is claimed is:
1. A method of separating a secondary alcohol compound from a primary alcohol compound comprising: providing a mixture of a secondary alcohol compound and a primary alcohol compound; reacting the mixture with an amount of an acylating agent of formula 1 sufficient to acylate the primary alcohol compound in the presence of an acid catalyst to form a partially acylated mixture comprising the secondary alcohol compound and acylated primary alcohol compound,

(1)

wherein $R^1$ is a bulky group selected from the group consisting of branched $C_{4-20}$ alkyl, $C_{5-20}$ cycloalkyl, substituted $C_{5-20}$ cycloalkyl, $C_{6-20}$ aryl, and substituted $C_{6-20}$ aryl; Y is selected from the group consisting of halogen, OH, and —O—C(O)—$R^1$; and separating the secondary alcohol compound from the acylated primary alcohol compound, the separated secondary alcohol compound being substantially free of the primary alcohol compound; wherein the acylation step is free of metal catalysts and enzymatic catalysts; and wherein the secondary alcohol compound is separated from the acylated primary alcohol compound by one or more of distillation, column chromatography, or crystallization.

2. The method of claim 1 wherein the mixture comprises a majority of the secondary alcohol compound and a minority of the primary alcohol compound.

3. The method of claim 1 wherein the acylating agent is present in ≥2 times the molar amount of the primary alcohol compound.

4. The method of claim 1 wherein the acid catalyst is present in an amount of 0.05 to 10 mole equivalents of the acylating agent.

5. The method of claim 1 wherein the secondary alcohol compound is separated from the acylated primary alcohol compound by fractional distillation.

6. The method of claim 1 wherein the secondary alcohol and primary alcohol compounds are isomers of a $C_{3-30}$ hydrocarbyl alcohol.

7. The method of claim 1 wherein the secondary alcohol and primary alcohol compounds are isomers.

8. The method of claim 1 wherein the partially acylated mixture further comprises an acylated secondary alcohol compound.

9. The method of claim 1 wherein the mixture of the secondary alcohol compound and the primary alcohol compound is a mixture of 1-methoxypropan-2-ol and 2-methoxypropan-1-ol.

10. The method of claim 1 wherein $R^1$ is selected from the group consisting of cyclopentyl, cyclohexyl, cycloheptyl, cyclooctyl, adamantyl, methyladamantyl, tert-butyl, neopentyl, 2-methyl-but-2-yl, 2,4-dimethylpent-3-yl, phenyl, methylphenyl, dimethylphenyl, trimethylphenyl, nitrophenyl, diphenylmethyl, naphthyl, and pyrenyl.

11. 1-Methoxypropan-2-ol having ≤10 ppm of 2-methoxypropan-1-ol.

12. Propylene glycol methyl ether acetate having ≤10 ppm of 2-methoxypropyl acetate.

* * * * *